(12) United States Patent
Cameron

(10) Patent No.: US 8,506,977 B2
(45) Date of Patent: Aug. 13, 2013

(54) CARAMEL-COATED INSECTICIDE

(76) Inventor: David Lynn Cameron, Port Orange, FL (US)

( * ) Notice: Subject to any disclaimer, the term of this patent is extended or adjusted under 35 U.S.C. 154(b) by 169 days.

(21) Appl. No.: 12/806,505

(22) Filed: Aug. 16, 2010

(65) Prior Publication Data

US 2011/0236449 A1    Sep. 29, 2011

(51) Int. Cl.
*A01N 25/32* (2006.01)
(52) U.S. Cl.
USPC ............ 424/406; 424/84; 424/405; 424/407; 424/409; 424/410; 424/659; 514/64

(58) Field of Classification Search
None
See application file for complete search history.

(56) References Cited

U.S. PATENT DOCUMENTS

| | | | | |
|---|---|---|---|---|
| 5,698,208 | A * | 12/1997 | Nigg et al. | 424/405 |
| 7,045,138 | B2 * | 5/2006 | Kennedy et al. | 424/406 |
| 7,264,827 | B1 * | 9/2007 | Malone et al. | 424/658 |
| 2010/0124560 | A1 * | 5/2010 | Hugerth et al. | 424/401 |

* cited by examiner

*Primary Examiner* — Neil Levy

(57) ABSTRACT

An insect bait comprising particles of an insect-killing compound onto which a coating of insect attracting material has been applied, and the method by which this bait is prepared.

1 Claim, No Drawings

CARAMEL-COATED INSECTICIDE

FIELD OF THE INVENTION

The current invention relates to baits used to control populations of insect pests, and to the methods used in the preparation of such baits.

BACKGROUND OF THE INVENTION

The use of baits to control the populations of insect pests is well known. To be effective, a bait must contain a compound that is lethal when ingested by an insect, and further, must attract the targeted types of insects and promote ingestion of a lethal amount of the insect-killing compound whenever the bait is encountered by a targeted insect. Most insect-killing compounds, including Boric Acid ($H_3BO_3$), are not themselves attractive to insects, and are not generally ingested by insects as food. This means that an effective insect bait must generally contain other compounds in addition to the insect-killing compound, the other compounds having the purpose of attracting insects and promoting ingestion of the insect-killing compound.

The use of Boric Acid as an insect-killing compound is well known in the prior art, the United States patent literature including the following documents: U.S. Pat. No. 1,636,688 (Harris, Jul. 26, 1927); U.S. Pat. No. 4,988,516 (Herring, Jan. 29, 1991); U.S. Pat. No. 1,029,203 (Jun. 11, 1912); and U.S. Pat. No. 4,438,090 (Brite, Mar. 20, 1984), and the foreign patent literature including the following: 0067209 (1984; JP); 0155303 (1984; JP); and 4654 (1899; GB). As an insect-killing compound, boric acid has the very significant advantages over alternative compounds of having very low toxicity toward humans and other mammals, and of low cost. Boric acid is not specifically attractive to insects, however, and is not generally regarded as food by insects. To take advantage of boric acid's insect killing properties, it must be incorporated into a bait with at least one other other compound that is attractive to insects, and that is regarded as food by insects.

Various bait compositions in which boric acid serves as the insect-killing component have been suggested. In the case of Herring (U.S. Pat. No. 4,988,516; 1988), it is recommended that boric acid be incorporated into a flat patty composed of white wheat flour, white vegetable shortening, chopped onions, white cane sugar, and water. While this formulation might be somewhat effective as an insect bait, it suffers from unnecessary complexity and relatively high cost. Patties must be replaced after only one month due to spoilage. The biggest drawback of this bait is that upon encountering a bait patty, an insect would have the option of ingesting some part of the patty, such as the chopped onion, while leaving the boric acid uningested. No insect bait in the prior art, whether using boric acid or some other compound for its insect-killing ability, accomplishes the critical tasks of attracting sweet-eating insects, and encouraging insects to ingest a lethal amount of the lethal compound upon every encounter with the bait, as effectively as the bait described by the current disclosure.

The current invention takes advantage of the unsurpassed ability of caramelized sugar to attract sweet-eating insects such as cockroaches, water bugs, and several types of ants. Further, caramelized sugar is a powerful feeding stimulus for these insects. Whenever a sweet-eating insect encounters small particles of boric acid coated with caramelized sugar, the caramel coating ensures that a lethal amount of the boric acid will be ingested by the insect. In addition to having unrivaled efficiency in killing sweet-eating insects, the current invention also has the advantages of being able to use boric acid as the insect-killing compound in the preferred embodiment, and of having a simple, low cost formulation.

SUMMARY

An improved insect bait is described comprising a composition in which a sweetening agent, such as caramelized sugar, is coated upon particles of an insect-killing compound, such as boric acid, the method for preparing such an insect bait being further disclosed.

DETAILED DESCRIPTION

In a preferred embodiment of the current invention, common solid table sugar is heated to cause its partial chemical decomposition and liquefication, this being referred to as caramelization of the sugar. As the caramelized sugar is cooled, liquid glycerin is added to prevent solidification. The liquid mixture of caramelized sugar and glycerin is mixed with solid boric acid in powder form, the small particles of the boric acid then being coated by the liquid mixture, producing a slightly sticky solid bait. Approximate proportions in which the compounds are used are as follows: 1 gram of table sugar, 2 milliliters of glycerin, and 10 grams of boric acid powder, producing approximately 13 grams of insect bait.

The bait thus formed resists spoilage and dehydration, and remains effective in killing sweet-eating insects for at least several months.

What is claimed is:

1. A method for preparing a bait composition to be used to control sweet-eating insect populations, said sweet-eating insects comprising cockroaches and some species of ants, comprising the steps of: preparing an attractant of sugar for said sweet-eating insects in liquid form, and coating particles of a compound of boric acid, lethal to said sweet-eating insects when ingested by them, with said liquid attractant and glycerol, the bait prepared by caramelization of the sugar by heating sugar to cause its partial chemical decomposition and liquefaction, followed by adding liquid glycerin to prevent solidification as the caramelized sugar is cooled, and then mixing with powdered boric acid, coating the boric acid with the liquid mixture, producing a solid bait.

* * * * *